United States Patent [19]

Fischer et al.

[11] 4,293,767
[45] Oct. 6, 1981

[54] APPARATUS FOR MEASURING THE THICKNESS OF THIN LAYERS

[76] Inventors: Helmut Fischer, Bergwaldstrasse 28, 7261 Gechingen; Albert Ott, Am Weinberg 22, 6200 Wiesbaden, Auringen; Willi Steegmüller, Tulpenstrasse 18, 7407 Rottenburg 15, all of Fed. Rep. of Germany

[21] Appl. No.: 69,610

[22] Filed: Aug. 24, 1979

[51] Int. Cl.³ ............................................. G01N 23/00
[52] U.S. Cl. ...................................... 250/308; 250/359
[58] Field of Search ............ 250/308, 307, 306, 358 R, 250/359, 360, 272

[56] References Cited

U.S. PATENT DOCUMENTS

| | | | |
|---|---|---|---|
| 3,493,755 | 2/1970 | Hannula | 250/308 |
| 3,714,436 | 1/1973 | Fischer | 250/308 |
| 4,115,690 | 9/1978 | Weinstock et al. | 250/308 |

Primary Examiner—Aflred E. Smith
Assistant Examiner—Carolyn E. Fields

[57] ABSTRACT

The apparatus measures the thickness of thin layers on strips and wires which are moved relative to the apparatus. The apparatus is stationary and includes one or more beta emitters directed towards the layer and spatially arranges relative to the longitudinal axis of a beta radiation detector or counting tube which is arranged to the rear of the beta emitter for counting the backscattered beta radiation, and a guide for the strip or wire at a specified distance from the beta emitter. The ratio of the characteristic cross-sectional dimension (D) of the window of the beta radiation detector to the intersecting surface diameter (d) of the intersecting surface layer/intensity distribution curve of the beta emitter, being expressed as D/d=15 . . . 2; with the distance between the layer and the beta radiation emitter being in the plateau region of the curve of the counting rate/distance characteristic obtained by the above feature.

14 Claims, 8 Drawing Figures

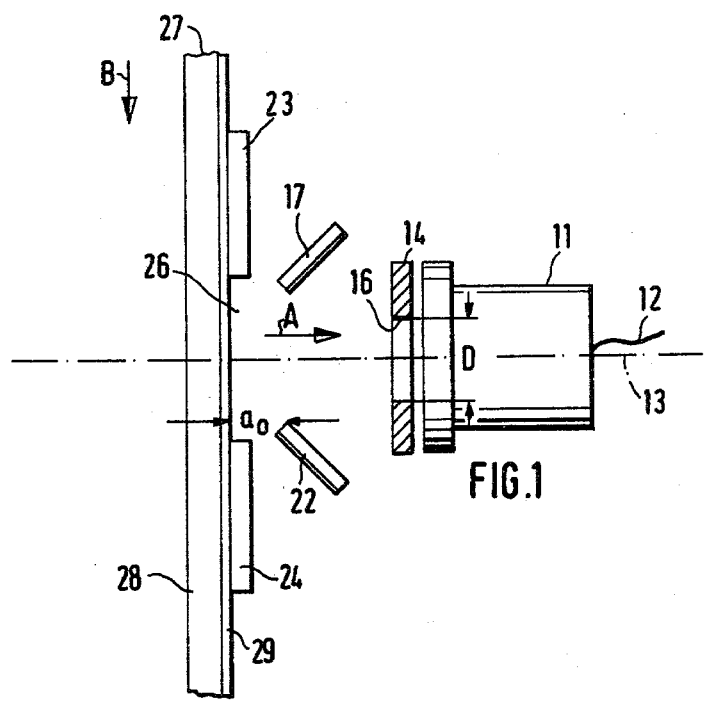
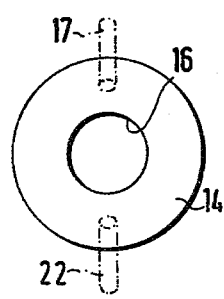
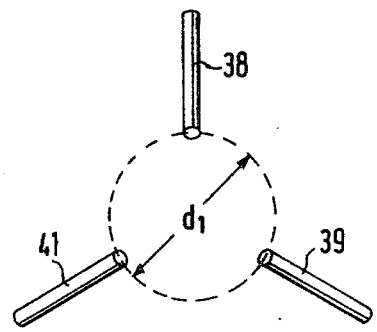

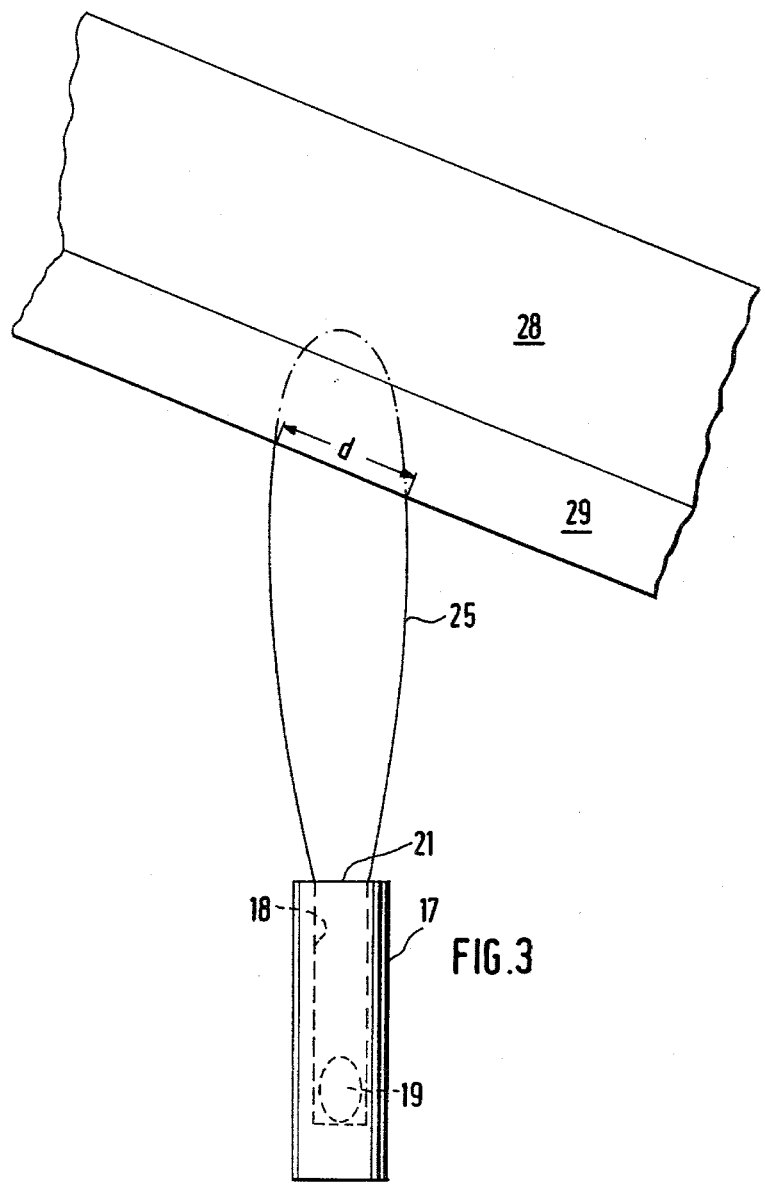

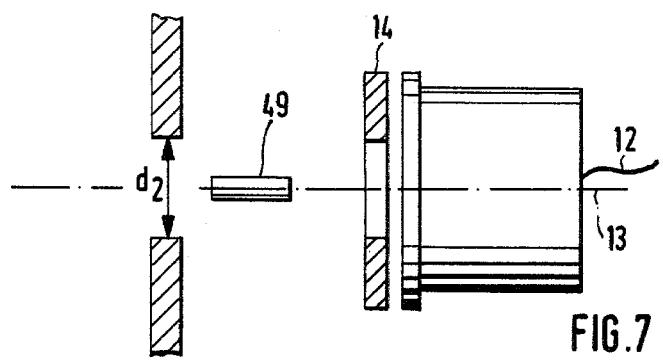
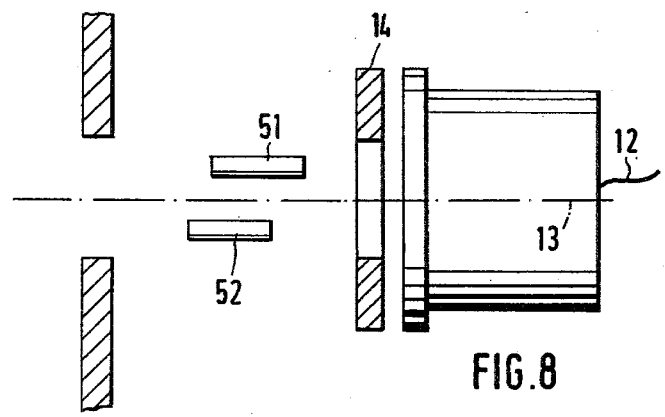

APPARATUS FOR MEASURING THE THICKNESS OF THIN LAYERS

The invention relates to an apparatus for measuring the thickness of thin layers on strip-shaped, wire-shaped or like material, which can be moved from a first point past the apparatus to a second point. The apparatus includes a beta radiator or emitter directed towards the layer and a counting tube arranged to the rear of the beta emitter for counting the backscattered beta radiation. The counting takes place while the material is being moved.

BACKGROUND OF THE INVENTION

Such an apparatus is known from U.S. Pat. No. 4,115,690. This apparatus has, inter alia, the following disadvantages:

1. The strip-shaped material is bent over repeatedly in the vicinity of the measuring instrument. The usually metallic material may be permanently deformed as a result. In this case the material is bent over repeatedly so that there is not only bending in one direction, but bending back and forth in both directions. This is also disadvantageous. If the material is then rewound onto a reel with torsion after measurement, detrimental forces can occur, as is known from twine or bobbins.

2. The measuring instrument rotates continuously. Therefore, the necessary inputs and outputs must be provided via slip rings.

3. The measuring time is limited. As beta radiation back scatter involves atomic statistics, the measuring precision can be increased by a sufficiently long measuring time. However, this is in principle impossible with the known instrument since the measuring time cannot commence until the material reaches the rotatable drum and must be terminated when the material is moved away from the measuring drum again. Therefore, in practice measurement is only possible over a time of about 270° of drum rotation and absolutely impossible for about 90° of the time.

4. Synchronizers must be provided to allow the measuring time to begin and end at the correct time.

5. In order that sufficient measured results may also be obtained, a plurality of beta emitters must rotate with the drum. However, to ensure that one beta emitter does not measure for a longer period than the others, the same length of measuring time determines that the beta emitters must be staggered through 180° when there are two such devices, by 120° when there are three beta emitters, etc.

6. In practice, at least two beta radiators must be provided to prevent the reading being merely a random test measurement.

7. The subsequently used computer must be equipped to process overlapping measuring times. In this respect also there are higher requirements than if only one beta radiator were to be used.

8. A really continuous reading is in this case merely replaced by a random test measurement, depending on the system. This method of measurement is not adapted to the measuring problem. If it is assumed, for example, that the instrument is intended for measuring copper-plated objects coming from a copper bath or gilded objects coming from a gilding bath, these units generally change their properties only at a slow rate, the time constants being in the region of at least a quarter of an hour. However, it is also characteristic for the coating to be suddenly defective at some point, but completely flawless to the left and right of said point. The known apparatus is not easily adapted for solving these problems.

9. If the beta radiator has detected a flaw, it must be determined which of the, if necessary, numerous beta radiators has detected the flaw.

10. The drum must have a comparatively large diameter to ensure careful treatment of the material. This creates design problems and, even when the instrument is installed in continuous production systems, this design results in disadvantages as there is usually very restricted space available in these systems.

11. If it is desired to measure strips or wires with the instrument, the known apparatus may be suitable as these materials are uniformly homogeneous. However, if it is desired to measure electric contacts which are in the form of punched-out strip, there is naturally sometimes one contact at one point and none at another point. It must therefore be ensured that the beta emitter is exactly opposite the contacts. This means that a quite special outer face of the drum is required for each measuring problem.

12. The known apparatus uses the known annular diaphragms or outer rings between the beta emitter and the material. Although these rings are made of a very hard material, they still wear. Moreover, particular care must be taken to ensure that the object to be measured is properly in contact with the annular diaphragms, otherwise erroneous readings are obtained.

13. Because the material is guided on the drum e.g. at 10 o'clock and guided off the drum at 7 o'clock, the first linearly advancing strip is not in alignment with the strip which is subsequently moved linearly off the drum. This staggered arrangement is in itself disadvantageous. However, as the material is under tension, this means that a component of a force is exerted on the apparatus at the same time.

OBJECT AND STATEMENT OF THE INVENTION

The object for the invention is to provide an apparatus of the initially mentioned type which avoids the disadvantages, and is cheap and the measuring principles of which can be adapted to the characteristics of the material to be measured.

This objective is achieved in accordance with the invention by the following features:

(a) The apparatus is stationary.
(b) The apparatus is provided with a guide for guiding the material at a definite distance from the beta radiator.
(c) The characteristic cross-sectional dimension (D) of the aperture of the beta radiation detector is in ratio to the sectional plane diameter (d) of the sectional plane layer/intensity distribution curve of the beta radiator, expressed as $D/d = 15 \ldots 2$.
(d) The distance between the coating and the beta radiator is in the plateau region of the counting rate/distance characteristic which is obtained by (c) above.

One great advantage of this arrangement is the plateau region obtained in the curve of the counting rate/distance characteristic. Another great advantage is the fact that the counting rate/distance characteristic curves are parallelized for different materials. For example, the counting rate/distance characteristic curves in respect of gold, nickel, platinum, etc. are now parallel for practical purposes. Therefore, one curve can be derived from the other merely by changing an additive factor. These advantages are observed in comparing U.S. Pat. No. 3,714,436. Moreover, advantageous results of the invention are achieved with the following features.

An even better plateau effect is achieved within the region indicated by D/d=10 . . . 4.

When beta radiation detectors having a larger window than that indicated by the proportional numbers are used, the window is covered by an outer ring which partially shields the window.

On account of this feature large beta radiation detectors can also be used. The outer ring makes it possible for the plateau effect to be further intensified and prevents shading or dimming by the small tube. In the case of Geiger-Müller tubes, for example, the large tubes are cheaper than the small tubes. No annular diaphragm or outer ring is required for the small tubes, but they are still costly.

The outer ring shows a possible way of using large, but cheap beta radiation detectors. With semiconductor beta radiation detectors it is exactly the opposite to G-M tubes. In this case the smaller ones are cheap and may be generally used without an outer ring, while the larger detectors are more costly and require an outer ring. It is a similar case with scintillation counters.

The beta emitter comprises an absorbing tube which is open on one side for emitting radiation. According to this feature a single tube is sufficient to achieve the plateau effect. The feature increases the plateau effect and reduces the measuring time. If n (tubes)=2, optimization is achieved with regard to expenditure and result obtained. Even a larger number of tubes would not bring about a substantial improvement by an order of magnitude (factor 10).

The tube is inclined relative to the geometric longitudinal axis of the beta radiation detector and directed at the geometric longitudinal axis and the layer. Through these features the tube is prevented from dimming backscattered beta particles, thereby also improving the plateau effect. The features simplify the design and possibly also mathematical treatment or usage.

n tubes in a spatially staggered arrangement relative to one another, are provided in a commonly irradiated area, n being greater than one. The features make it possible for the plateau effect to be improved, the layer or coating to be exposed to the maximum number of beta particles and at the same time for the maximum number of beta particles to be scattered back to the flaw detector tube.

The stagger is 360°/n. The features make it possible to achieve a spatially identical staggered arrangement and therefore uniform exposure to radiation and better conditions for data processing. Also, the feature simplifies the design and the possibility mathematical processing.

The angle to the geometric longitudinal axis is between 30° and 60°, and preferably between 40° and 50°. The angle sizes improve the plateau effect. Uniform measuring principles are achieved.

The angles of all the tubes are equal. A simple construction, a more uniform irradiation and a configuration which is simpler for data processing are achieved. The feature can also achieve the plateau effect, the optimum in terms of expenditure/result being obtained by using two tubes.

The emitters of all the beta emitters are of the same type and all the beta emitters have the same parameters.

The features have the same effect. As the features described immediately above.

A plurality of beta emitters are arranged parallel to and around the geometric longitudinal axis, the emitters being spaced at variable intervals from the layer. The plateau effect in these embodiments may also be improved by the features.

The beta emitter comprises a surface emitter concentric with the longitudinal axis, with its radiation emitting surface being directed at the geometric longitudinal axis and the layer. The features enable the measuring time to be reduced and the plateau to be broadened somewhat.

The carrier for the surface emitter serves at the same time as an outer ring for the beta radiation detector. The features enable the diaphragm or outer ring to be used at the same time as a carrier for the radionuclides.

The number of backscattered beta particles absorbed by the beta radiation (counting tube) pass back through the diaphragm or outer ring. However, this is of no consequence with this kind of measuring problem since the material is in any case continuously coated and since moreover the characteristics of the coating systems have high time constants, e.g. the thickness of the coating varies only slowly so that long measuring times can be used.

DESCRIPTION OF THE DRAWINGS

The invention will now be described with the aid of preferred embodiments. In the drawings:

FIG. 1 is a diagrammatic side view showing an apparatus according to the invention, in partial section, and a coated material, FIG. 2 is a view of the annular diaphragm in the direction of arrow A shown in FIG. 1, with tubes indicated by dot-and-dash lines, FIG. 3 is a substantially enlarged side view of a tube, showing a hole and an inserted radionuclide, the intensity distribution curve and intersection with the coated material, FIG. 5 is a view, in the direction of arrow A, of tubes in a three-dimensional arrangement, but without an annular diaphragm and counting tube, FIG. 7 is a side view similar to FIG. 1, but without showing the material or coating when only one tube is used, FIG. 8 is a view similar to FIG. 7, but showing two tubes in a staggered arrangement.

DETAILED DESCRIPTION

Figure 4:
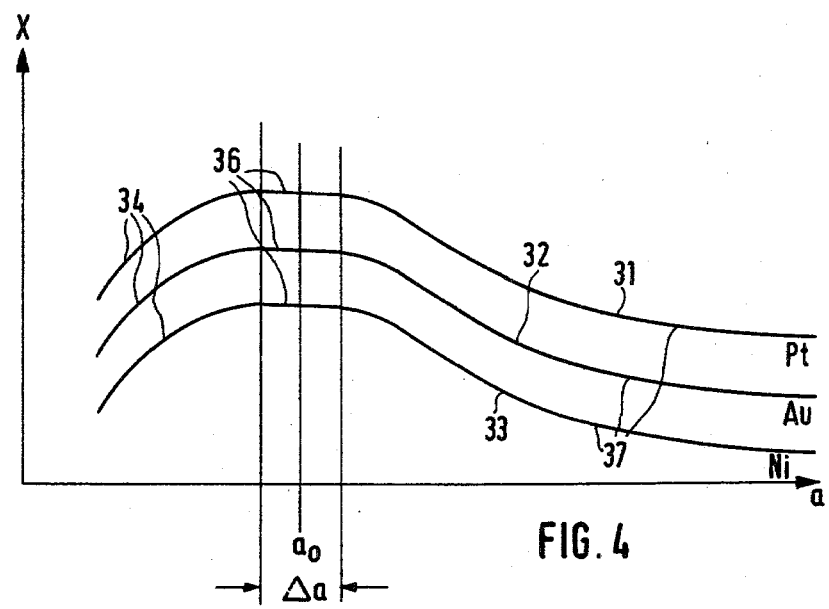
FIG. 4 shows the curve path with a slightly broadened plateau region which can be achieved with the invention.

As shown in FIGS. 1 and 2 a conventional type of G-M tube 11 (Geiger-Müller tube) comprises an output 12 which generates a pulse in a known manner whenever beta particles pass from the left into the G-M tube 11 in the direction of arrow A, for example. The G-M tube 11 is arranged coaxially with a geometric longitudinal axis 13. An annular diaphragm 14 made of beta radiation-absorbing material is provided in front of the window of the G-M tube 11. The annular diaphragm 14 has a coaxial and preferably circular aperture and is rigidly connected to the G-M tube 11.

As shown in FIG. 3, a tube 17 is made of a beta-absorbing material and has a blind hole, 18 in the bottom of which is situated a radionuclide 19. The beta rays can be emitted from the aperture 21, but because of the geometry of this beta radiation device only a very thin pencil ray is emitted. The tube 17 is rigidly mounted (in a manner not shown) together with the G-M tube 11 and the diaphragm 14, that is, so that it is inclined at an angle of approximately 45° to the longitudinal axis 13, allowing the rays to be emitted at the bottom left end of the tube.

A second identical tube 22 is arranged below the first tube 17, lying at an angle of 45° to the longitudinal axis 13 and accordingly emitting radiation from the top left end. The tubes 17 and 22 lie in the plane of the drawing of FIG. 1 and have the same mirror-image geometry relative to the longitudinal axis 13 and therefore also to the ring 16 and G-M tube 11.

A guide 23, 24 is rigidly connected to the aforementioned parts (in a manner not shown) and, like these, is also stationary; the guide can, for example, be made from a section of plastic material and symmetrically arranged relative to the geometric longitudinal axis 13 at least in the vicinity thereof. An intermediate free space 26 is left between the guides 23, 24. The radionuclides of the tubes 17,22 emit rays into part of the free space 26.

To the left of the guide 23, 24 there is provided a strip 27 made of a material 28 provided with a coating 29. The coating or layer 29 is in contact with the guide 23, 24 and is irradiated with beta rays from the tubes 17, 22. The strip 27 is moved in a straight line in the direction of arrow B. It could also be moved antiparallel to arrow B or it could be moved in either of the directions perpendicular to the plane of the drawing in FIG. 1. The strip 27 can be solid or it can also take the form of punched-out parts not yet separated from the strip, such as e.g. contact springs or the like. The strip 27 can also be in the form of a wire which can have a circular, oval or the like cross section. The material 28 can be, for example, copper and the coating 29 gold, for example. The material 28 does not always have to be thicker than the coating 29. On the contrary, the material 28 can have an infinitely variable thickness in practice in view of the backscatter properties of the coating 29 or alternatively it can have zero thickness.

There is a distance $a_o$ between the layer 29 and the top of tube 17 or 22. As shown in FIG. 1, this distance is measured perpendicular to the layer 29. It is immaterial whether the distance $a_o$ is measured from the right or the left bounding surface of the layer 29 since the layer thickness in relation to the distance $a_o$ is negligible.

The distance $a_o$ is plotted as the abscissa a in FIG. 4 and the counting rate X as the ordinate. The counting rate is the number of pulses obtained from the output 12 after a predetermined time. Curve 31 is associated with a layer of platinum, curve 32 with a layer of gold and curve 33 with a layer of nickel. Each of these curves 31, 32, 33 has an ascending branch 34, extending to the right into a plateau 36 and leading even further to the right into a descending branch 37. For the sake of clarity the plateaus 36 are shown somewhat broader. Therefore, when the layers are of equal thickness, the counting rate for platinum is higher than that for gold because platinum has a higher atomic weight. The same applies to the ratio of nickel to gold, on the one hand, and nickel to platinum, on the other.

If this diagram is compared with FIG. 8 from German Pat. No. 20 13 270, corresponding to U.S. Pat. No. 3,714,436 and British Pat. No. 1,323,906, the first difference to be noticed is that there are plateaus 36 in the diagram according to the invention and the second difference is that the curves 31, 32, 33 can be derived from one another by parallel translation.

The distance $a_o$ lies at the centre of the plateau region 36. If the layer 29 now varies by delta a/2, this has no effect on the counting rate X. This characteristics is important because in many practical cases the layer 29 does not always have the distance $a_O$. Variations can occur because, for example, the layer 29 has a surface pattern, but the guide 23, 24 guides the layer 29, as it were, over the mountain peaks. However, variations in distance can also be due to the fact that the stamped and/or punched-out parts are not always in exact alignment, when seen in the direction of arrow B. These variations in distance can be considerably greater than the thickness of the layer. However, the distance variation is not inconvenient as a result of the plateaus 36.

With practical embodiments the distance variations delta a can be in the region of 0.4 to 0.6 mm. In practical cases the value of $a_o$ is 0.1 to 1.5 mm.

It is naturally also very convenient for subsequent mathematical calculation of the counting rate X if the curves 31, 32, 33 are substantially parallel displaced curves, and particularly in the delta a region in question. The counting rate contains information as to the thickness of the layer 29.

FIG. 5 shows diagrammatically how tubes 38, 39, 41 would have to be arranged, if the number of tubes=3, in order to obtain the simplest possible conditions for construction and data analysis. Irregular angular distances are naturally also possible. They are 120° in the illustrated case. The angle of inclination of the tubes 38, 39, 41 is in this case also 45°. However, the tubes could also be arranged at more acute or more obtuse angles.

Figure 6:
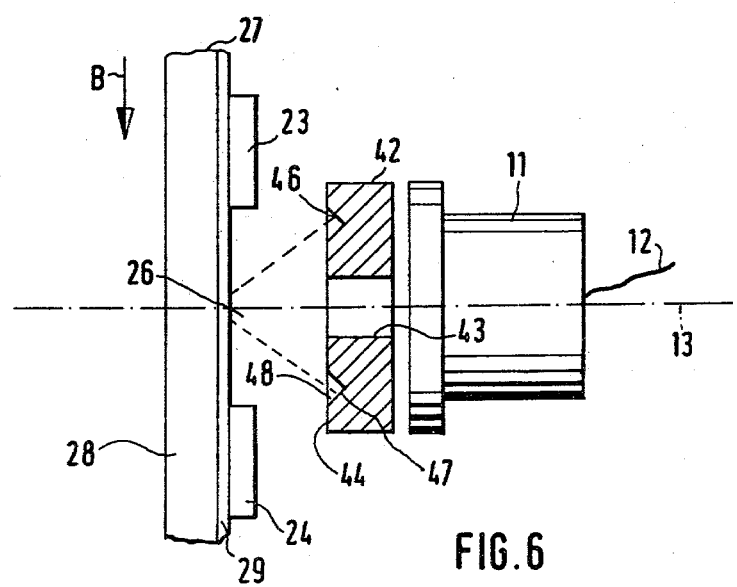
FIG. 6 is a view similar to FIG. 1, but showing a surface emitter combined with the outer ring.

According to FIG. 6 there is provided an annular diaphragm or outer ring 42 which also has a coaxial, circular aperture 43 and partially shields the G-M tube 11 on the left. In this case a coaxial V-shaped groove 46 is provided in the left front side 44. The outer edge of this groove is in this case coated with radionuclide material 48 which faces the free space 26 and can emit radiation in the direction thereof. In this case also the diaphragm or ring 42 is rigidly connected to the G-M tube 11 and the guide 23, 24.

Better results are obtained both with the arrangements shown in FIG. 5 and in FIG. 6 than with the arrangement shown in FIG. 1. However, this improvement does not amount to an order of magnitude, particularly in view of the fact that the invention permits long measuring times.

A single tube 49 is arranged coaxially in the embodiment shown in FIG. 7. However, the tube 49 does not have to be coaxial in all cases. It can also be arranged at an angle, like the tube 17, for example.

In this connection it should be stressed once more that the free space 26 is in no way equivalent to the previously known diaphragms or outer rings which, according to the above mentioned reference, for example, limit the measuring surface. In the case of the invention there is no limitation of the measuring surface which would be comparable with known measuring surface limitation.

As shown in FIG. 8, the plateau effect and parallelization may also be achieved by two tubes 51, 52 arranged parallel to the longitudinal axis, but staggered at intervals. It can be imagined that this figure originated from FIG. 1, the angle of the tubes 17, 22 to the longitudinal axis being reduced to zero and in addition the tubes 17, 22 being in a staggered arrangement.

Another variation can be derived from FIG. 5: in this case also the angle to the longitudinal axis is zero and the three tubes are staggered at three different intervals. Even then the plateau effect and parallelization are achieved.

A characteristic path according to FIG. 4 is obtain even when one or several emitters are used, but when the diaphragm or ring 14 is completely omitted and small G-M tubes or small semiconductor detectors are used.

The thin pencil of rays mentioned at the beginning can be designated as the intensity distribution curve 25 which is rotationally symmetrical with respect to the geometric longitudinal axis illustrated. This curve is therefore a space curve. It is club-shaped similar to the lobes which are used for aerial navigation are known both from the V.H.F. range, etc. In a stable state both the broken and unbroken parts indicate the intensity distribution curve. However, the intensity distribution curve 25 intersects the layer 29 in the embodiment shown in FIG. 1 at an angle of 45°. The intersection ellipse has a diameter d. The aperture 16 has a diameter D, and these are the values D/d=15 . . . 2 and advantageously D/d=10 . . . 4. The value of d is not quite exact. It would only be exact if the layer 29 were perpendicular to the geometric longitudinal axis. Also, the intensity distribution curve 25 is not a precisely plottable curve on account of the statistical processes required with emitters.

By way of approximation the value d can also be replaced by the value $d_1$ as indicated in FIG. 5. In this case it is the diameter of the circle which can be described through the aperture 21 of all the tubes. If two tubes lying opposite one another were used, the value $d_1$ could be determined in the same way.

Alternatively, the value $d_2$ can be adopted by approximation, as indicated in FIG. 7. This is the diameter of the free space 26.

In a practical embodiment d is equal to 3 mm, and D 8 mm, a G-M tube with a window diameter of 18 mm being used.

In practice 0 to 70% will be shielded depending on the size of the G-M tube. In the simplest example the aperture 16 will be circular. However, it could also be square, and the characteristic cross-sectional dimension D would then be the edge length of the square. The aperture 16 and the free space 26 are usually circular because this aperture is easy to produce. The outer ring or diaphragm will be provided as close as possible to the beta radiation detector. The best arrangement is for the ring to be attached directly to the detector (G-M tube).

According to past experience the optimum distance between the G-M tube/outer ring unit and the layer 29 is approximately 1 to 4 mm.

In practice Delta a=0.4 to 0.6 mm. In practice $a_O$ is approximately 0.1 to 1.5 mm. This can mean that the left branch in the curve path of FIG. 4 ceases to exist.

What I claim is:

1. In an apparatus for measuring the thickness of a thin layer on strip-shaped, wire-shaped or like material, which can be moved from a first point past the apparatus to a second point, comprising a beta emitter directed towards said thin layer and a windowed beta radiation detector arranged to the rear of the beta emitter for counting the backscattered beta radiation, the counting taking place while the material is being moved, the improvement wherein:
   (a) the apparatus is stationary;
   (b) the apparatus is provided with a guide for guiding the material at a specified distance from the beta emitter;
   (c) the ratio of the characteristic cross-sectional dimension (D) of the window of the beta radiation detector, to the intersecting surface diameter (d) of the intersecting surface layer/intensity distribution curve of the beta emitter, being expressed as D/d coming within the range 15 . . . 2;
   (d) the distance between the layer and the beta emitter is in the plateau region of the counting rate/distance characteristic which is obtained by (c) above.

2. Apparatus as claimed in claim 1, wherein D/d comes within the range 10 . . . 4.

3. Apparatus as claimed in claim 1 or 2, wherein when beta radiation detectors having a larger window than that indicated by the proportional numbers D/d are used, the window is covered by an outer ring which partially shields the window.

4. Apparatus as claimed in claim 1, wherein the beta emitter comprises an absorbing tube which is open on one side for emitting radiation.

5. Apparatus as claimed in claim 4, wherein the tube is inclined relative to the geometric longitudinal axis of the beta radiation detector and directed at the geometric longitudinal axis and the layer.

6. Apparatus as claimed in claim 5, wherein n tubes in a spatially staggered arrangement relative to one another, are provided in a commonly irradiated area, n being greater than one.

7. Apparatus as claimed in claim 6, wherein the stagger is 360°/n.

8. Apparatus as claimed in claim 6, wherein the angles of all the tubes relative to the geometric longitudinal axis of the beta radiation detector are equal.

9. Apparatus as claimed in claim 4, wherein the angle of said absorbing tube to the geometric longitudinal axis of the beta radiation detector is between 30° and 60°.

10. Apparatus as claimed in claim 4, wherein the angle of said absorbing tube to the geometrical longitudinal axis of the beta radiation detector is between 40° and 50°.

11. Apparatus as claimed in claim 1 or 4, wherein a plurality of beta emitters are arranged parallel to and around the geometric longitudinal axis of the beta radiation detector, the emitters being spaced at variable intervals from the layer.

12. Apparatus as claimed in claim 1 comprising a plurality of emitters, all the beta emitters being of the same type and all the beta emitters having the same parameters.

13. Apparatus as claimed in claim 1, wherein the beta emitter comprises a surface emitter concentric with the longitudinal axis of the beta radiation detector, with its radiation emitting surface being directed at the geometric longitudinal axis and the layer.

14. Apparatus as claimed in claim 13, wherein the carrier for the surface emitter serves at the same time as an outer ring for the beta radiation detector.

* * * * *